(12) United States Patent
Ebata

(10) Patent No.: US 11,534,143 B2
(45) Date of Patent: Dec. 27, 2022

(54) ACOUSTIC WAVE DIAGNOSTIC APPARATUS AND CONTROL METHOD OF ACOUSTIC WAVE DIAGNOSTIC APPARATUS

(71) Applicant: FUJIFILM Corporation, Tokyo (JP)

(72) Inventor: Tetsurou Ebata, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 183 days.

(21) Appl. No.: 16/725,640

(22) Filed: Dec. 23, 2019

(65) Prior Publication Data

US 2020/0129160 A1 Apr. 30, 2020

Related U.S. Application Data

(63) Continuation of application No. PCT/JP2018/020629, filed on May 30, 2018.

(30) Foreign Application Priority Data

Aug. 23, 2017 (JP) .............................. JP2017-160260

(51) Int. Cl.
*A61B 8/00* (2006.01)
*G06T 7/13* (2017.01)
(Continued)

(52) U.S. Cl.
CPC .............. *A61B 8/54* (2013.01); *A61B 5/0095* (2013.01); *A61B 8/085* (2013.01); *A61B 8/463* (2013.01);
(Continued)

(58) Field of Classification Search
CPC ......... A61B 8/54; A61B 5/0095; A61B 8/085; A61B 8/463; A61B 8/467; A61B 8/5261;
(Continued)

(56) References Cited

U.S. PATENT DOCUMENTS

| 2006/0052704 A1* | 3/2006 | Baba ...................... A61B 8/488 600/453 |
| 2012/0078103 A1* | 3/2012 | Tashiro ................... A61B 8/54 600/443 |

(Continued)

FOREIGN PATENT DOCUMENTS

| CN | 105050504 A | 11/2015 |
| JP | 2011-104194 A | 6/2011 |

(Continued)

OTHER PUBLICATIONS

International Preliminary Report on Patentability and English translation of the Written Opinion of the International Searching Authority (PCT/IB/326, PCT/IB/373 and PCT/ISA/237) dated Mar. 5, 2020 for Application No. PCT/JP2018/020629.

(Continued)

*Primary Examiner* — Keith M Raymond
*Assistant Examiner* — Adam D. Kolkin
(74) *Attorney, Agent, or Firm* — Birch, Stewart, Kolasch & Birch, LLP

(57) ABSTRACT

An ultrasound diagnostic apparatus includes: a display unit that displays an acoustic wave image; an operation unit for a user to perform an input operation; a measurement item designation receiving unit that receives designation of a measurement item relevant to a measurement target; a detection measurement algorithm setting unit that sets a detection measurement algorithm based on the measurement item; a position designation receiving unit that receives designation of a position of a measurement target on the acoustic wave image; a measurement unit that detects the measurement target from the acoustic wave image based on the position of the measurement target and the detection measurement algorithm, measures the measurement target, calculates a measurement candidate, and displays the measurement candidate on the display unit; and a measurement (Continued)

candidate designation receiving unit that receives designation of the measurement candidate in a case where a plurality of measurement candidates are displayed.

14 Claims, 7 Drawing Sheets

(51) Int. Cl.
A61B 5/00 (2006.01)
A61B 8/08 (2006.01)
(52) U.S. Cl.
CPC .......... *A61B 8/467* (2013.01); *A61B 8/5261* (2013.01); *G06T 7/13* (2017.01); *G06T 2207/10132* (2013.01); *G06T 2207/30004* (2013.01)
(58) Field of Classification Search
CPC ............ G06T 7/13; G06T 2207/10132; G06T 2207/30004
See application file for complete search history.

(56) References Cited

U.S. PATENT DOCUMENTS

| | | | |
|---|---|---|---|
| 2013/0012835 A1* | 1/2013 | Chono | A61B 8/467 600/587 |
| 2014/0236010 A1* | 8/2014 | Nakano | A61B 8/464 600/440 |
| 2015/0320399 A1 | 11/2015 | Chono et al. | |
| 2017/0014105 A1 | 1/2017 | Chono | |

FOREIGN PATENT DOCUMENTS

| | | |
|---|---|---|
| JP | 2014-64708 A | 4/2014 |
| JP | 2015-156960 A | 9/2015 |
| WO | WO 2014/155825 A1 | 10/2014 |
| WO | WO 2016/190256 A1 | 12/2016 |

OTHER PUBLICATIONS

International Serarch Report (PUT/ISA/210) dated Aug. 21, 2018, far Application No. PCT/JP2018/020629, along with an English translation.

Extended European Search Report, dated Jul. 10, 2020, for corresponding European Application No. 18848309.3.

Chinese Office Action and Search Report for corresponding Chinese Application No. 201880045912.7, dated Dec. 27, 2021, with an English translation.

Chinese Office Action for corresponding Chinese Application No. 201880045912.7, dated Aug. 26, 2022, with an English translation.

* cited by examiner

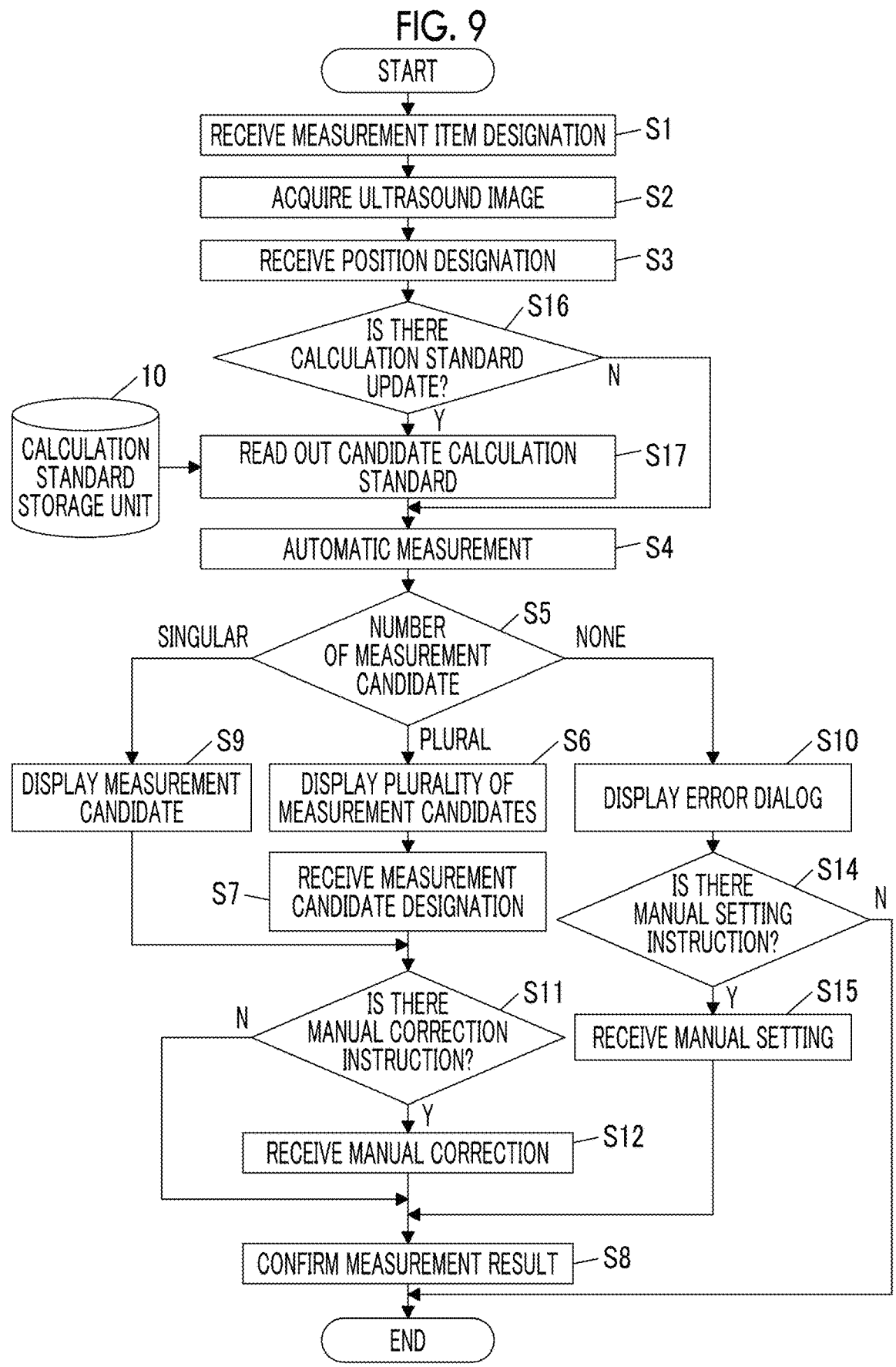

ACOUSTIC WAVE DIAGNOSTIC APPARATUS AND CONTROL METHOD OF ACOUSTIC WAVE DIAGNOSTIC APPARATUS

CROSS-REFERENCE TO RELATED APPLICATIONS

This application is a Continuation of PCT International Application No. PCT/JP2018/020629 filed on May 30, 2018, which claims priority under 35 U.S.C. § 119(a) to Japanese Patent Application No. 2017-160260 filed on Aug. 23, 2017. Each of the above application(s) is hereby expressly incorporated by reference, in its entirety, into the present application.

BACKGROUND OF THE INVENTION

1. Field of the Invention

The present invention relates to an acoustic wave diagnostic apparatus and a control method of an acoustic wave diagnostic apparatus and in particular, to an acoustic wave diagnostic apparatus and a control method of an acoustic wave diagnostic apparatus for measuring a part on an acoustic wave image.

2. Description of the Related Art

In recent years, medical acoustic diagnostic apparatuses generally have a measurement function for measuring the length, size, area, and the like of various organs, lesions, and the like included in an acquired acoustic wave image. In order to measure a measurement target, a user usually operates a caliper, that is, a cursor using an input device for inputting coordinates, such as a track pad, a track ball, and a mouse, to set a measurement point, a region of interest, and the like on a display image. As described above, in a case where a manual operation is performed by the user, there is an influence due to the user's experience, skill level, and the like. Therefore, various attempts have been made to automate the manual operation by the user.

For example, JP2015-156960A discloses that an ultrasound diagnostic apparatus extracts the shape, position, and the like of a characteristic part in an image by performing image recognition on a tomographic image of the target tissue, automatically specifies the Doppler measurement position in the target tissue based on the extracted part, and automatically specifies the Doppler measurement position based on the blood flow speed in the target tissue.

JP2011-104194A discloses that an ultrasound diagnostic apparatus performs image recognition on an acquired ultrasound image to automatically specify the position of an ultrasound probe with respect to the blood vessel at the time of acquisition of the ultrasound image and to automatically calculate the average inner diameter of blood vessels from the ultrasound image.

SUMMARY OF THE INVENTION

Incidentally, the image quality of an ultrasound image often changes depending on the subject and the imaging conditions, such as the position and the angle of the ultrasound probe and imaging parameters. For this reason, image recognition for the ultrasound image may fail. In JP2015-156960A and JP2011-104194A, image recognition is used to automate various operations. However, in a case where the image recognition fails, there is a problem that an erroneous result is output and this increases the burden on the user.

The present invention has been made in order to solve such a conventional problem, and it is an object of the present invention to provide an acoustic wave diagnostic apparatus and a control method of an acoustic wave diagnostic apparatus capable of performing reliable measurement with reduced burden on a user in automatic measurement of a measurement target.

In order to achieve the aforementioned object, an acoustic wave diagnostic apparatus of the present invention comprises: a display unit that displays an acquired acoustic wave image; an operation unit for a user to perform an input operation; a measurement item designation receiving unit that receives designation of a measurement item relevant to a measurement target from the user through the operation unit; a detection measurement algorithm setting unit that sets a detection measurement algorithm based on the measurement item received by the measurement item designation receiving unit; a position designation receiving unit that receives designation of a position of the measurement target on the acoustic wave image displayed on the display unit from the user through the operation unit; a measurement unit that detects the measurement target from the acoustic wave image based on the position of the measurement target received by the position designation receiving unit and the detection measurement algorithm set by the detection measurement algorithm setting unit, measures the detected measurement target, calculates a measurement candidate, and displays the measurement candidate on the display unit; and a measurement candidate designation receiving unit that receives designation of the measurement candidate from the user through the operation unit in a case where a plurality of the measurement candidates are displayed on the display unit. The measurement candidate received by the measurement candidate designation receiving unit is used as a measurement result.

It is preferable that the measurement candidate includes at least one of a measurement line used for measurement or a measurement value calculated for the measurement target, and the measurement line is displayed so as to be superimposed on the acoustic wave image.

The measurement line is, for example, a line segment connecting two measurement points disposed at an edge of the measurement target or a closed curve drawn along the edge of the measurement target.

The measurement unit may detect the measurement target by recognition based on image processing, calculate a reliability of a recognition result based on at least one of edge likeness of the acoustic wave image at an end point of the line segment or a distance from the position of the detected measurement target received by the position designation receiving unit to the line segment, and display a plurality of the measurement candidates selected according to the calculated reliability on the display unit.

The measurement unit may detect the measurement target by recognition based on image processing, calculate a reliability of a recognition result based on edge likeness of the acoustic wave image at an edge of the closed curve, and display a plurality of the measurement candidates selected according to the calculated reliability on the display unit.

The measurement unit may change at least one of a color, a thickness, a line type, or a transparency for displaying the plurality of measurement candidates according to a value of the calculated reliability.

The measurement unit may display both the plurality of measurement lines and the plurality of measurement values so as to be associated with each other in at least one of the color, the thickness, the line type, or the transparency.

A calculation standard storage unit that stores a predetermined calculation standard may be further provided, and the measurement unit may calculate the measurement candidate based on the calculation standard stored in the calculation standard storage unit.

A calculation standard update unit that updates the calculation standard stored in the calculation standard storage unit based on a reliability corresponding to the measurement candidate received by the measurement candidate designation receiving unit may be further provided.

A manual correction receiving unit that receives correction of the measurement candidate calculated by the measurement unit from the user through the operation unit may be further provided.

A calculation standard update unit that updates the calculation standard stored in the calculation standard storage unit based on at least one of a reliability corresponding to the measurement candidate received by the measurement candidate designation receiving unit or correction of the measurement candidate received by the manual correction receiving unit may be further provided.

The measurement unit may highlight the measurement candidate on the display unit in a case where a measurement value of the measurement candidate calculated by the measurement unit is outside a predetermined measurement standard range.

The measurement item designation receiving unit may receive designation of at least one of a name of the measurement target, a name of a lesion, a name and measurement content of the measurement target, or a name and measurement content of a lesion as a measurement item relevant to the measurement target.

The acoustic wave image may be any one of an ultrasound image, a photoacoustic wave image, or a composite image of an ultrasound image and a photoacoustic wave image.

A control method of an acoustic wave diagnostic apparatus of the present invention comprises: receiving designation of a measurement item relevant to a measurement target from a user; setting a detection measurement algorithm based on the received measurement item; displaying an acoustic wave image; receiving designation of a position of the measurement target on the acoustic wave image from the user; detecting the measurement target from the acoustic wave image based on the received position of the measurement target and the set detection measurement algorithm, measuring the detected measurement target, and calculating and displaying a measurement candidate; receiving designation of the measurement candidate from the user in a case where a plurality of the measurement candidates are displayed; and using the received measurement candidate as a measurement result.

According to the present invention, the acoustic wave diagnostic apparatus comprises the measurement candidate designation receiving unit that receives the designation of a measurement candidate from the user through the operation unit in a case where a plurality of measurement candidates are displayed on the display unit, and the measurement candidate received by the measurement candidate designation receiving unit is used as a measurement result. Therefore, even in a case where image recognition fails, it is possible to perform reliable measurement with reduced burden on the user.

BRIEF DESCRIPTION OF THE DRAWINGS

FIG. 9 is a flowchart showing second and subsequent measurement operations of the ultrasound diagnostic apparatus according to the fourth embodiment of the present invention.

DESCRIPTION OF THE PREFERRED EMBODIMENTS

Hereinafter, embodiments of the present invention will be described with reference to the accompanying diagrams.

First Embodiment

Figure 1:
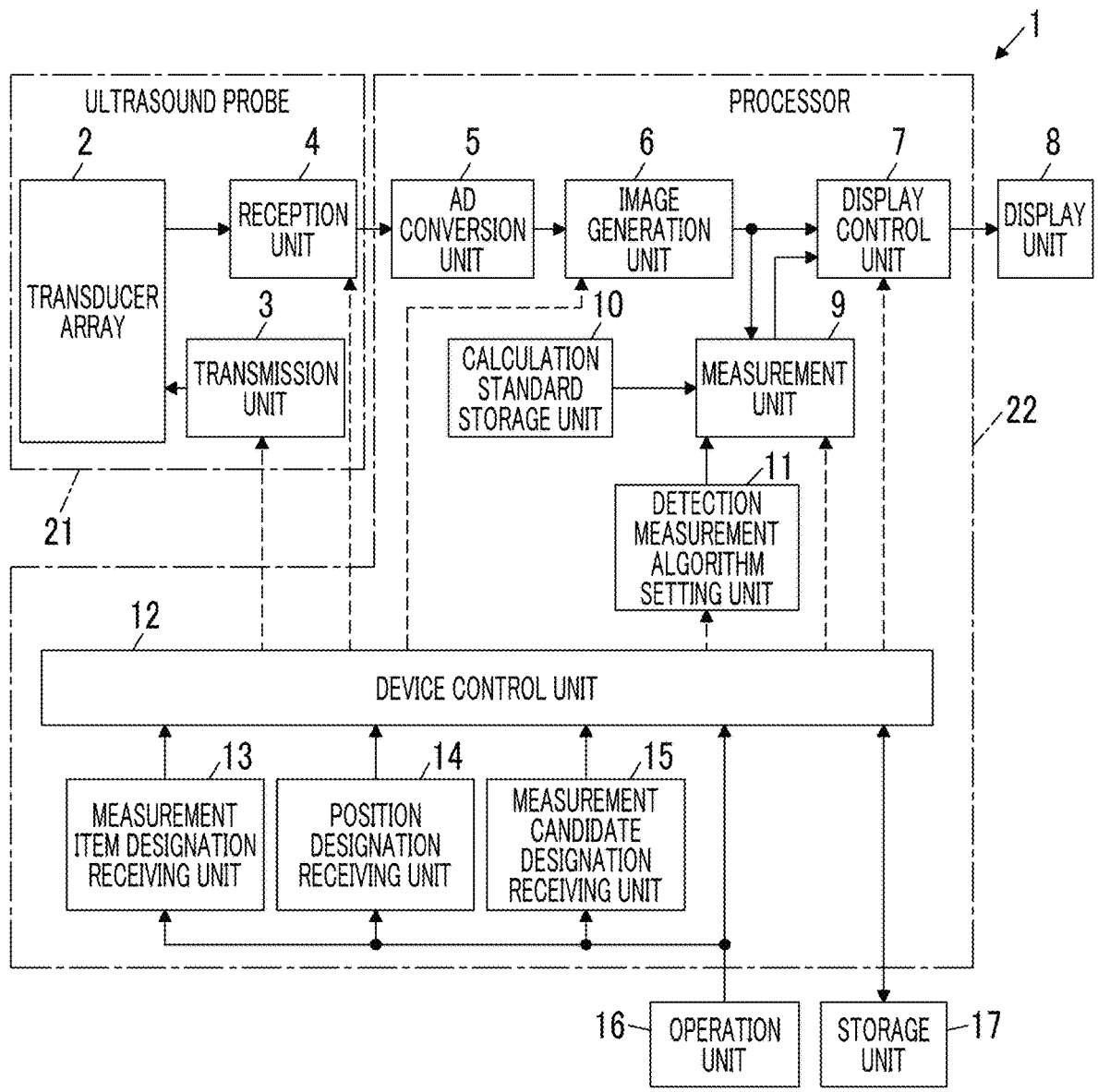
FIG. 1 is a block diagram showing the configuration of an ultrasound diagnostic apparatus according to a first embodiment of the present invention.

FIG. 1 shows the configuration of an ultrasound diagnostic apparatus 1 according to a first embodiment of the present invention. As shown in FIG. 1, the ultrasound diagnostic apparatus 1 comprises a transducer array 2, and a transmission unit 3 and a reception unit 4 are connected to the transducer array 2. An analog digital (AD) conversion unit 5, an image generation unit 6, a display control unit 7, and a display unit 8 are sequentially connected to the reception unit 4. A measurement unit 9 is connected to the image generation unit 6, and a calculation standard storage unit 10 is connected to the measurement unit 9. A detection measurement algorithm setting unit 11 is connected to the measurement unit 9.

A device control unit 12 is connected to the transmission unit 3, the reception unit 4, the image generation unit 6, the display control unit 7, the measurement unit 9, and the detection measurement algorithm setting unit 11. A measurement item designation receiving unit 13, a position designation receiving unit 14, a measurement candidate designation receiving unit 15, an operation unit 16, and a storage unit 17 are connected to the device control unit 12. The operation unit 16 is connected to the measurement item designation receiving unit 13, the position designation receiving unit 14, and the measurement candidate designation receiving unit 15. The device control unit 12 and the storage unit 17 are connected to each other so that information can be transmitted and received bidirectionally.

An ultrasound probe 21 is configured by the transducer array 2, the transmission unit 3, and the reception unit 4, and a processor 22 is configured by the AD conversion unit 5, the image generation unit 6, the display control unit 7, the measurement unit 9, the calculation standard storage unit 10, the detection measurement algorithm setting unit 11, the device control unit 12, the measurement item designation receiving unit 13, the position designation receiving unit 14, and the measurement candidate designation receiving unit 15.

The transducer array 2 of the ultrasound probe 21 shown in FIG. 1 has a plurality of elements (ultrasound transducers) arranged in a one-dimensional or two-dimensional manner. According to a driving signal supplied from the transmission unit 3, each of the elements transmits an ultrasound wave and receives a reflected wave from a subject and outputs a reception signal. For example, each element is formed by using a transducer in which electrodes are formed at both ends of a piezoelectric body formed of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

The transmission unit 3 of the ultrasound probe 21 includes, for example, a plurality of pulse generators. Based on a transmission delay pattern selected according to the control signal from the device control unit 12, the transmission unit 3 adjusts the amount of delay of each driving signal so that ultrasound waves transmitted from the plurality of elements of the transducer array 2 form an ultrasound beam, and supplies the obtained signals to the plurality of elements. Thus, in a case where a pulsed or continuous-wave voltage is applied to the electrodes of the elements of the transducer array 2, the piezoelectric body expands and contracts to generate pulsed or continuous-wave ultrasound waves from each transducer. From the combined wave of these ultrasound waves, an ultrasound beam is formed.

The transmitted ultrasound beam is reflected by a target, for example, a part of the subject, and propagates toward the transducer array 2 of the ultrasound probe 21. The ultrasound waves propagating toward the transducer array 2 in this manner are received by the respective elements configuring the transducer array 2. In this case, the respective transducers configuring the transducer array 2 expand and contract by receiving the propagating ultrasound waves, thereby generating electric signals. These electric signals are output, as reception signals of the ultrasound waves, from each transducer to the reception unit 4. Although not shown, the reception unit 4 has an amplification unit for amplifying an ultrasound reception signal input from each transducer. In a case where the amplified signal is converted into digitized element data by the AD conversion unit 5, the element data is output to the image generation unit 6.

Figure 2:
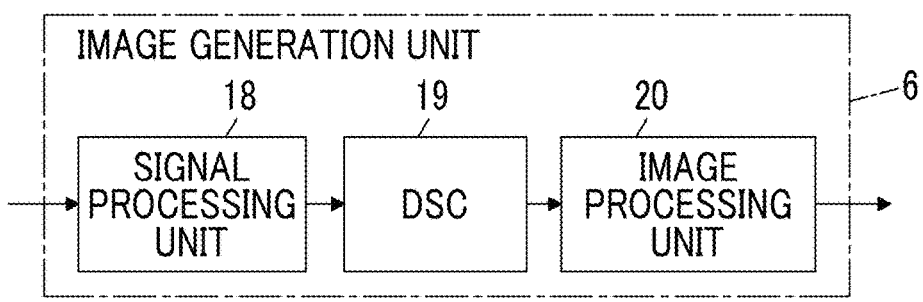
FIG. 2 is a block diagram showing the internal configuration of an image generation unit in the first embodiment of the present invention.

As shown in FIG. 2, the image generation unit 6 of the processor 22 has a configuration in which a signal processing unit 18, a digital scan converter (DSC) 19, and an image processing unit 20 are connected in series to each other. Based on a reception delay pattern selected according to the control signal from the device control unit 12, the signal processing unit 18 performs reception focusing processing in which delays are given to respective pieces of element data according to the set sound speed and addition (phasing addition) is performed. Through the reception focusing processing, a sound ray signal with narrowed focus of the ultrasound echo is generated. The signal processing unit 18 generates a B mode image signal, which is tomographic image information regarding tissues inside the subject, by correcting the attenuation of the generated sound ray signal due to the propagation distance according to the depth of the reflection position of the ultrasound wave and then performing envelope detection processing. The B mode image signal generated as described above is output to the DSC 19.

The DSC 19 raster-converts the B mode image signal into an image signal according to the normal television signal scanning method. The image processing unit 20 performs various kinds of necessary image processing, such as brightness correction, gradation correction, sharpness correction, and color correction, on the image data obtained in the DSC 19, and then outputs the B mode image signal to the display control unit 7 and the measurement unit 9. The measurement unit 9 will be described in detail later.

The operation unit 16 of the ultrasound diagnostic apparatus 1 is for the user to perform an input operation, and can be configured to comprise a keyboard, a mouse, a track pad, a touch panel, and the like.

The measurement item designation receiving unit 13 of the processor 22 receives designation of a measurement item relevant to the measurement target from the user through the operation unit 16.

The measurement item relevant to the measurement target is an item that can indicate at least one of the measurement target or the measurement content, and the measurement target can include a name of a target part such as an organ, a name of a lesion such as a tumor, a cyst, and a hemorrhage, and an item relevant to abnormalities. The measurement content can include the length, area, and the like of the measurement target. Therefore, for example, the measurement item can include any one of only the name of a measurement target, only the name of a lesion, only the item relevant to abnormalities, the name of a measurement target and its measurement content, the name of a lesion and its measurement content, or an item relevant to abnormalities and its measurement content. In a case where the measurement item includes only the measurement target, for example, the measurement content, such as whether the length is to be measured or the size is to be measured for the measurement target designated by the user through the operation unit 16, is associated therewith. Specifically, for example, a table in which the measurement target and the measurement content are associated with each other is stored in the storage unit 17, an external memory (not shown), or the like, and the measurement content corresponding to the measurement target is selected based on this table.

The position designation receiving unit 14 of the processor 22 receives designation of the position of a measurement target on the ultrasound image displayed on the display unit 8 from the user through the operation unit 16.

The detection measurement algorithm setting unit 11 sets an algorithm for detecting the measurement target and an algorithm for measuring the measurement target based on the measurement item that the measurement item designation receiving unit 13 has received from the user through the operation unit 16. In general, the algorithm for detecting the measurement target on the image differs depending on the type of the measurement target, such as an organ and a lesion. The algorithm for measuring the measurement target on the image differs depending on the measurement content, such as the measurement of the length and the measurement of the area of the measurement target. The detection measurement algorithm setting unit 11 stores an algorithm corresponding to each measurement target and an algorithm corresponding to each measurement content as an association table, and sets a detection measurement algorithm with reference to the association table in a case where the measurement item designation receiving unit 13 receives a measurement item from the user through the operation unit 16.

As the detection measurement algorithm, a known algorithm that is generally used can be used. Here, the algorithm defines calculation means for achieving the purpose, such as detection and measurement. For example, the algorithm is implemented as a software program in an apparatus and is executed by a central processing unit (CPU).

For example, for the algorithm for detecting the measurement target, there is a method in which typical pattern data is stored in advance as a template, a pattern data similarity is calculated while searching for an image with a template, and it is considered that a measurement target is present in a place where the similarity is equal to or greater than a threshold value and is the maximum. For the calculation of the similarity, in addition to simple template matching, for example, a machine learning method described in Csurka et al.: Visual Categorization with Bags of Keypoints, Proc. of ECCV Workshop on Statistical Learning in Computer Vision, pp. 59-74 (2004) or a general image recognition method using deep learning described in Krizhevsk et al.: ImageNet Classification with Deep Convolutional Neural Networks, Advances in Neural Information Processing Systems 25, pp. 1106-1114 (2012) can be used.

In a case where the position designation receiving unit 14 receives the designation of the position of the measurement target from the user through the operation unit 16, the measurement unit 9 of the processor 22 detects the measurement target based on the received position and the detection measurement algorithm set by the detection measurement algorithm setting unit 11, performs measurement for the detected measurement target, and calculates a measurement candidate and displays the measurement candidate on the display unit 8. Here, the measurement candidate includes at least one of a measurement line used for measurement of the measurement target or a measurement value calculated for the measurement target. In a case where the measurement line is displayed on the display unit 8, the measurement line is displayed so as to be superimposed on the ultrasound image. The measurement unit 9 determines the position of a detection range for detecting the measurement target based on the position designated by the user through the operation unit 16, and detects the measurement target in the determined detection range. The size of the detection range can be set in advance, and the setting can be changed by the user through the operation unit 16.

In addition, the measurement unit 9 calculates a measurement candidate based on the calculation standard stored in advance in the calculation standard storage unit 10. In this case, a plurality of measurement candidates may be calculated.

In a case where a plurality of measurement candidates are calculated by the measurement unit 9 and displayed on the display unit 8, the measurement candidate designation receiving unit 15 of the processor 22 receives designation of a measurement candidate from the user through the operation unit 16. For example, in a case where a plurality of measurement lines are displayed on the display unit 8 so as to be superimposed on the ultrasound image and the user selects one measurement lines through the operation unit 16, the measurement candidate designation receiving unit 15 receives that a measurement candidate including the selected measurement line has been designated.

The display control unit 7 of the ultrasound diagnostic apparatus 1 generates a composite image by combining the image data generated by the image generation unit 6 with the measurement candidate and the measurement result calculated by the measurement unit 9, and displays the composite image on the display unit 8.

The display unit 8 includes, for example, a display device, such as a liquid crystal display (LCD), and displays an ultrasound image under the control of the device control unit 12.

The device control unit 12 controls each unit of the ultrasound diagnostic apparatus 1 based on a command input by the user through the operation unit 16.

The storage unit 17 stores an operation program and the like of the ultrasound diagnostic apparatus 1, and recording media, such as a hard disc drive (HDD), a solid state drive (SSD), a flexible disc (FD), a magneto-optical disc (MO), a magnetic tape (MT), a random access memory (RAM), a compact disc (CD), a digital versatile disc (DVD), a secure digital card (SD card), and a universal serial bus memory (USB memory), or a server can be used.

The AD conversion unit 5, the image generation unit 6, the display control unit 7, the measurement unit 9, the calculation standard storage unit 10, the detection measurement algorithm setting unit 11, the device control unit 12, the measurement item designation receiving unit 13, the position designation receiving unit 14, and the measurement candidate designation receiving unit 15 are configured by a CPU and a control program causing the CPU to execute various kinds of processing. However, these may also be configured by digital circuits. The AD conversion unit 5, the image generation unit 6, the display control unit 7, the measurement unit 9, the calculation standard storage unit 10, the detection measurement algorithm setting unit 11, the device control unit 12, the measurement item designation receiving unit 13, the position designation receiving unit 14, and the measurement candidate designation receiving unit 15 can also be integrated partially or entirely into one CPU.

Figure 3:
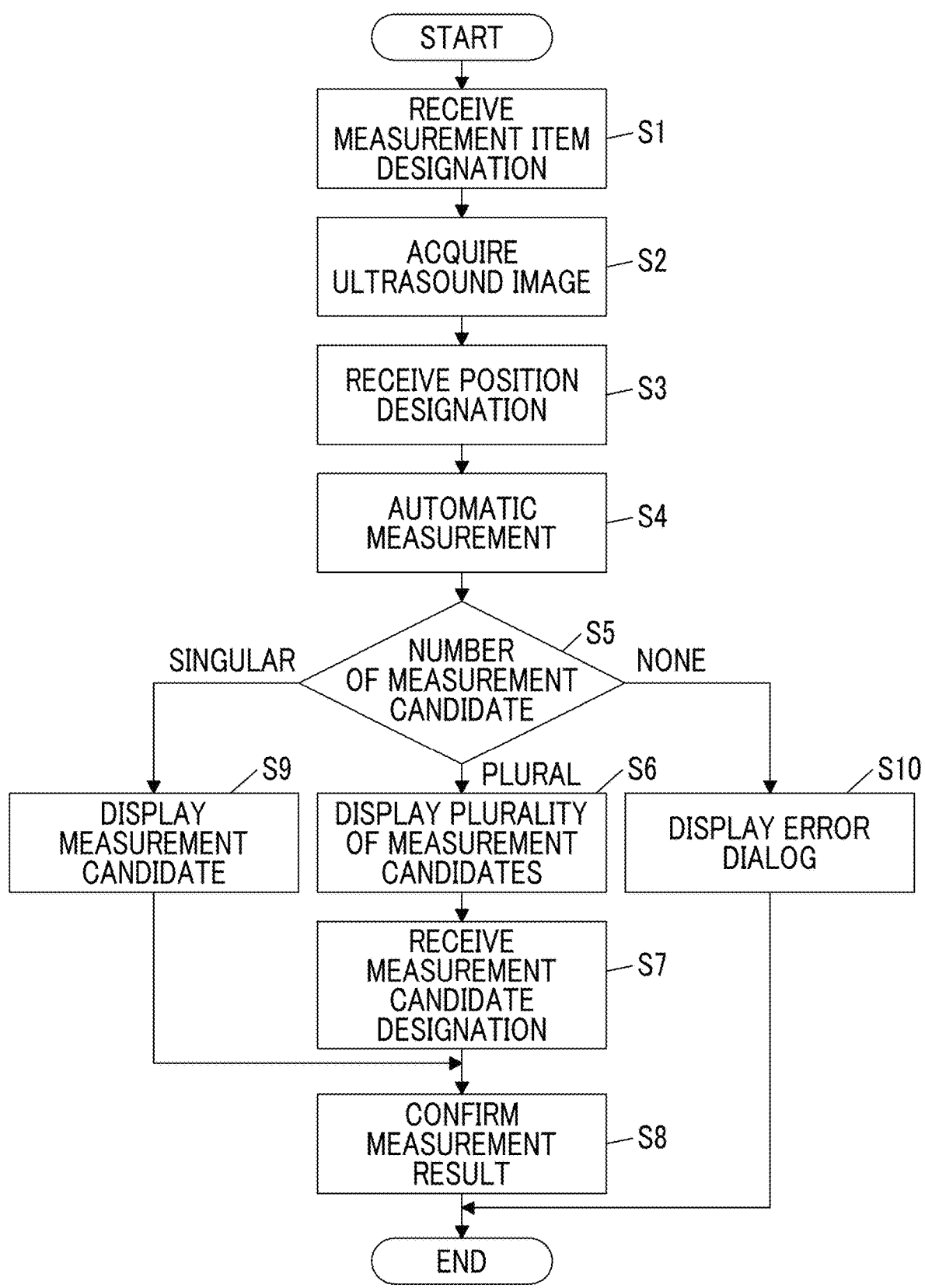
FIG. 3 is a flowchart showing a measurement operation of the ultrasound diagnostic apparatus according to the first embodiment of the present invention.

Next, the measurement operation of the ultrasound diagnostic apparatus 1 according to the first embodiment will be described with reference to the flowchart shown in FIG. 3.

First, in step S1, the measurement item designation receiving unit 13 receives a measurement item designated by the user through the operation unit 16. For example, in a case where a measurement operation in ultrasound diagnostic apparatus 1 is started, a list of measurement items is displayed on the display unit 8, so that one of the plurality of measurement items displayed in the list can be selected by the user through the operation unit 16. As described above, in a case where the designation of the measurement item is received, the detection measurement algorithm setting unit 11 sets a detection measurement algorithm according to the designated measurement item.

Then, in step S2, the ultrasound diagnostic apparatus 1 acquires an ultrasound image. As the ultrasound image, an image captured on the spot using the ultrasound probe 21 can be used, and an image acquired from an external memory (not shown) can also be used.

In subsequent step S3, the position designation receiving unit 14 receives designation of the position of a measurement target on the ultrasound image displayed on the display unit 8 from the user through the operation unit 16. In the case of designating the position of the measurement target, for example, the user may designate one point in a region showing the measurement target. In a case where the designation of the position of the measurement target is received as described above, the process proceeds to step S4.

In subsequent step S4, automatic measurement is performed on the measurement item designated in step S1.

First, the measurement unit 9 detects a measurement target by recognition based on image processing on the basis of the detection measurement algorithm set by the detection measurement algorithm setting unit 11 in step S1 and the position of the measurement target designated in step S3. For example, in a case where the measurement item designated in step S1 is the gallbladder, the measurement unit 9 sets a detection range for the ultrasound image acquired in step S2 based on the detection measurement algorithm and the position of the gallbladder designated in step S3, and detects an image of the gallbladder within the set detection range.

In this case, the measurement unit 9 determines the size of the detection range of the measurement target according to the measurement item designated by the user in step S1, and determine the position of the detection range according to the position of the measurement target designated by the user in step S3. In addition, the measurement unit 9 determines the detection order of the measurement target based on the measurement item and the position designated by the user in step S3. For example, although not shown, in a case where the measurement item is relevant to a round cross section such as the short axis diameter of the gallbladder and the short axis diameter of the abdominal aorta, detection of the measurement target is sequentially performed along a spiral scanning line that extends from the center to the outside with the position designated by the user as the center.

Then, the measurement unit 9 sets a measurement line to be used for measurement of the detected measurement target, and calculates the reliability of the recognition result based on image processing for the measurement line. In this case, the measurement unit 9 calculates the reliability using the reliability calculation standard stored in the calculation standard storage unit 10.

For example, in the case of measuring the length of the gallbladder on the ultrasound image, the measurement unit 9 extracts a plurality of line segments whose end points are disposed on the boundary surrounding the gallbladder region on the ultrasound image, that is, the edge of the gallbladder, and calculates the reliability based on the edge likeness of the ultrasound image at the end point for each line segment.

The measurement line to be used for measurement of the detected measurement target is set based on the rule determined according to the measurement item by the detection measurement algorithm. For example, in a case where the measurement item is the length of the long axis of the gallbladder, line segments having two end points disposed on the inner wall of the gallbladder region are extracted as measurement lines in the longest order. In a case where the measurement item is the diameter of the abdominal aorta, line segments having two end points, which pass through the center of gravity of the abdominal aorta and are disposed on the outer wall of the abdominal aorta, are extracted as measurement lines in the longest order.

The edge likeness indicates the contour likeness in the target part on the image, and the reliability based on the edge likeness of the image at a target point can be calculated by image recognition using, for example, the contrast between the target point and surrounding points.

Then, the measurement unit 9 determines measurement line candidates suitable for measurement based on the calculated reliability and the calculation standard stored in the calculation standard storage unit 10. As a method for determining measurement line candidates, for example, a number of measurement lines determined in descending order of reliability can be set as candidates, a measurement line whose reliability is equal to or higher than a threshold value can be set as a candidate, a measurement line having reliability equal to or greater than the product of the highest reliability and a defined percentage can be set as a candidate, and a combination of these methods can be adopted.

Finally, the measurement unit 9 calculates a measurement value for each of the measurement line candidates determined in this manner. For example, in a case where the measurement line is a line segment whose end points are disposed at the edge of the measurement target, the length of each measurement line determined as a candidate is measured.

In subsequent step S5, the measurement unit 9 determines whether a plurality of measurement lines have been determined as candidates in step S4, whether one measurement line has been determined as a candidate, or there is no measurement line determined as a candidate. In a case where it is determined that a plurality of measurement lines have been determined as candidates in step S5, the process proceeds to step S6.

Figure 4:
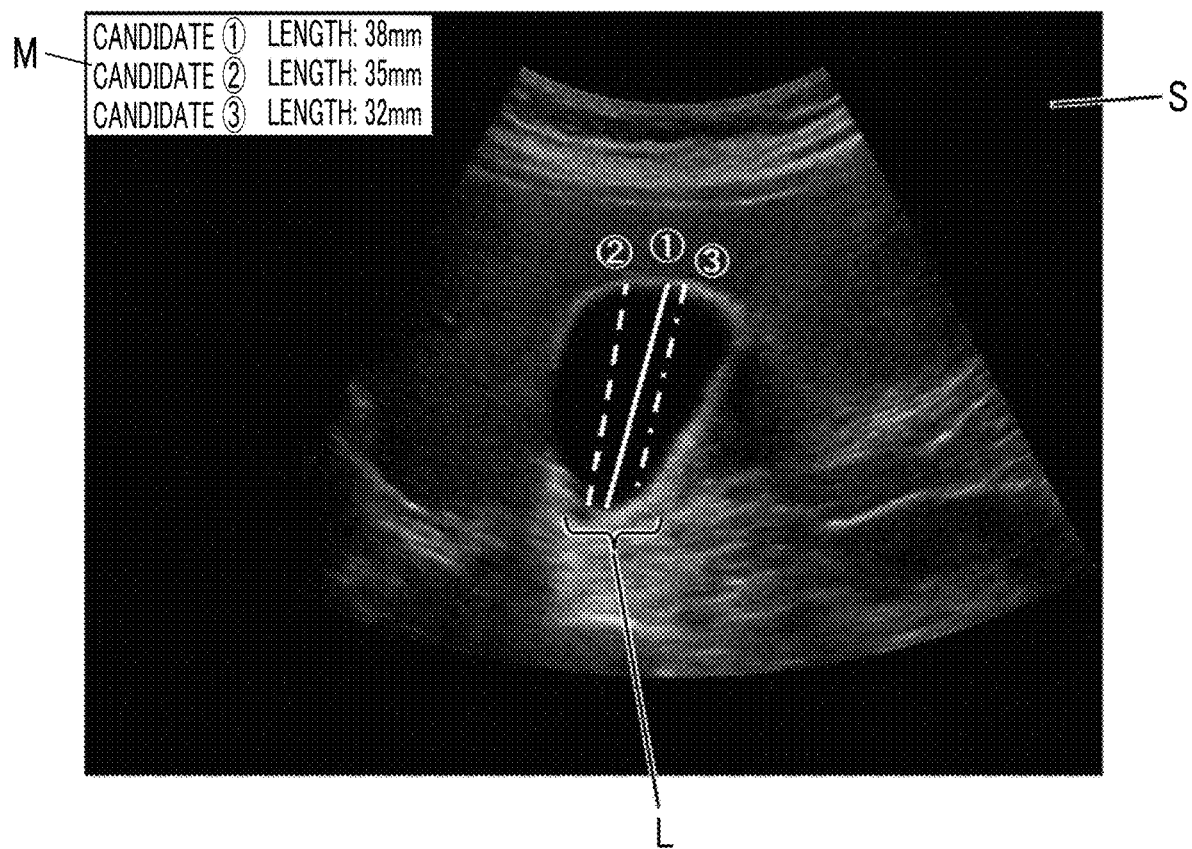
FIG. 4 is a diagram showing a display example of a measurement candidate in the first embodiment of the present invention.

In step S6, the measurement unit 9 transmits a command to the display control unit 7 so that a plurality of measurement candidates are displayed on the display unit 8. Here, the measurement candidate includes at least one of a plurality of measurement lines used for measurement or a plurality of measurement values corresponding to the respective measurement lines. In a case where both the measurement line and the corresponding measurement value are included, for example, display shown in FIG. 4 is performed on the display unit 8. That is, on the display unit 8, a plurality of measurement lines L are displayed so as to be superimposed on an ultrasound image S, and a plurality of measurement values corresponding to the plurality of measurement lines L are displayed as a list M.

Thus, in a case where a plurality of measurement candidates are displayed on the display unit 8, one of the plurality of measurement candidates is designated by the user through the operation unit 16 in step S7. In a case where one measurement candidate is designated by the user through the operation unit 16, the measurement candidate designation receiving unit 15 receives this designation result.

In subsequent step S8, the measurement candidate designated by the user through the operation unit 16 in step S7 is confirmed as the measurement result, and the measurement operation in the ultrasound diagnostic apparatus 1 ends.

In a case where it is determined that only one measurement line has been determined as a candidate in step S5, the process proceeds to step S9. In step S9, the measurement unit 9 transmits a command to the display control unit 7 so that the determined measurement candidate is displayed on the display unit 8. Accordingly, in a case where the measurement candidate is displayed on the display unit 8 so as to be superimposed on the ultrasound image, the process proceeds to step S8 in which the measurement candidate displayed on the display unit 8 is confirmed as the measurement result, and the measurement operation in the ultrasound diagnostic apparatus 1 ends.

In a case where it is determined that there is no measurement line determined as a candidate in step S5, the process proceeds to step S10. In step S10, an error dialog indicating that there is no measurement line as a candidate is displayed on the display unit 8, and the measurement operation in the ultrasound diagnostic apparatus 1 ends.

According to the ultrasound diagnostic apparatus 1 of the first embodiment described above, in a case where a plurality of measurement line candidates are determined in automatic measurement for the measurement target, the plurality of measurement candidates are displayed on the display unit 8, and one measurement candidate is designated by the user through the operation unit 16. Therefore, it is possible to obtain a reliable measurement result while reducing the burden on the user.

In the first embodiment of the present invention, the ultrasound diagnostic apparatus 1 performs measurement of a measurement target on the ultrasound image. However, the measurement may also be performed on an acoustic wave image other than the ultrasound image. For example, the ultrasound diagnostic apparatus 1 may also perform measurement of a measurement target on a photoacoustic wave image and a composite image obtained by superimposing an ultrasound image and a photoacoustic wave image.

As an example of the measurement line used for the automatic measurement in step S4, a line segment having the edge of the measurement target as an end point is mentioned. However, a closed curve drawn along the edge of the measurement target may be used as the measurement line, and the cross-sectional area of the measurement target may be measured by calculating the area of a portion surrounded by the closed curve. In this case, the reliability may be calculated based on the edge likeness of the ultrasound image in the closed curve drawn along the edge of the measurement target. A method of determining a measurement line candidate using the calculated reliability is the same as that in a case where the measurement line is a line segment.

Although the reliability of each line segment is calculated based on the edge likeness of the ultrasound image at the end point of the line segment used for measurement of the measurement target in step S4, the reliability calculation method is not limited to this. For example, the reliability may be calculated so as to have a higher value as a distance between the point designated by the user through the operation unit 16 in step S3 and each line segment used for measurement of the measurement target becomes shorter and have a lower value as the distance becomes longer.

Alternatively, a sum, an average value, or the like of the reliability calculated based on the edge likeness of the ultrasound image at the end point of the line segment used for measurement of the measurement target and the reliability calculated using a plurality of methods, such as the reliability calculated based on the distance between the line segment and the point designated by the user may be determined as the final line segment reliability.

In step S4, a plurality of measurement targets may be detected in the ultrasound image. In this case, in the case of calculating the reliability of a plurality of measurement lines, a composite reliability for each measurement line may be calculated based on the reliability of the measurement target superimposed on each measurement line and the reliability of the measurement line calculated based on the edge likeness of the ultrasound image.

For example, in a case where the gallbladder size is designated as a measurement item in step S1 and a plurality of measurement targets are detected in step S4, the measurement unit 9 calculates a similarity with respect to the pattern data of the gallbladder, which is stored in advance, as the reliability of the measurement target by performing image recognition such as template matching for each measurement target. In addition, the measurement unit 9 may calculate the reliability of a plurality of measurement lines based on the edge likeness in the ultrasound image at the end points of the line segments, which are measurement lines, and calculate the sum or product of the reliability of the measurement lines and the reliability of the measurement target, on which the measurement lines are superimposed, as a composite reliability for each measurement line.

In this case, the measurement unit 9 extracts measurement candidates based on the composite reliability for each measurement line.

In a case where measurement lines and measurement values are displayed as a plurality of measurement candidates in step S6, the measurement unit 9 may display the measurement values arranged in descending order of reliability from the measurement value of the measurement line with high reliability. By displaying a plurality of measurement values in this manner, the user can easily select a measurement line with high reliability.

In step S6, the measurement unit 9 may change at least one of the color, thickness, line type such as a solid line and a broken line, or transparency for displaying a plurality of measurement candidates according to the calculated reliability value. In addition, the measurement unit 9 may display both a plurality of measurement lines and a plurality of corresponding measurement values so as to be associated with each other in at least one of the color, thickness, line type, or transparency. In this manner, in a case where the user visually recognizes a plurality of measurement candidates, it becomes easy to check the measurement line and the measurement value in association with each other.

In order to prevent the display on the display unit 8 from becoming complicated due to a large number of measurement items displayed on the display unit 8 in step S1 and a large number of measurement candidates displayed on the display unit 8 in step S6, an upper limit may be set for the number of measurement items and the number of measurement candidates displayed at one time on the display unit 8. For example, only a predetermined number of measurement items or measurement candidates may be displayed on the display unit 8, and the measurement items and the measurement candidates may be appropriately switched and displayed by the user operation through the operation unit 16.

Figure 5:
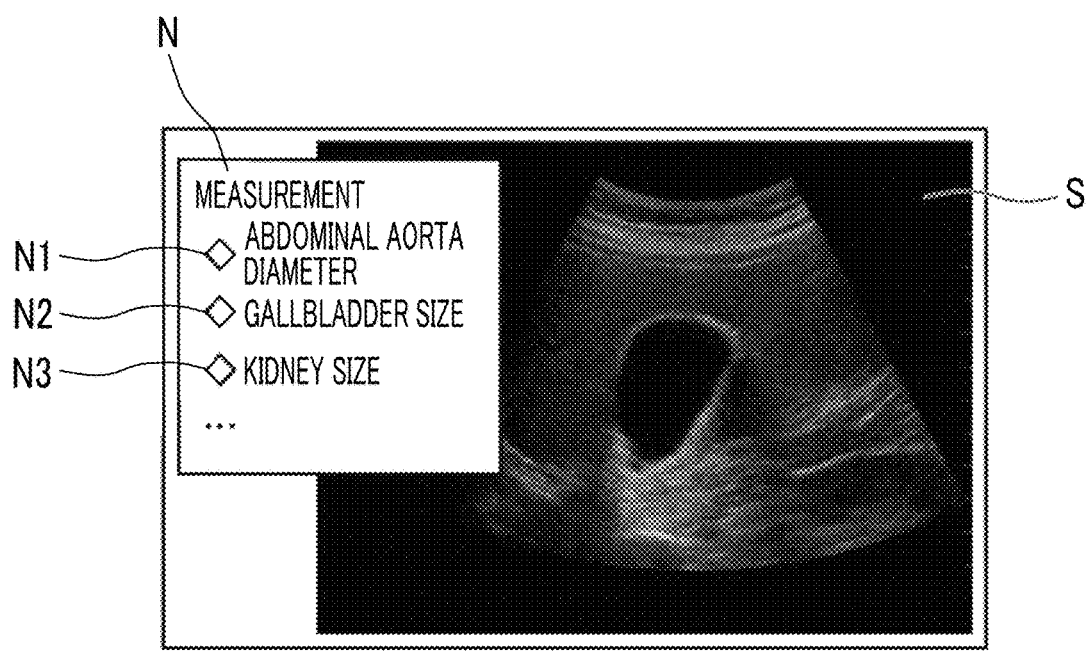
FIG. 5 is a diagram showing a display example of a list of measurement items in the first embodiment of the present invention.

In the measurement operation of the ultrasound diagnostic apparatus 1, after receiving the designation of the measurement item in step S1, the process proceeds to step S2 to acquire an ultrasound image. However, the designation of the measurement item may be received after acquiring the ultrasound image. In this case, for example, as shown in FIG. 5, in a case where the measurement operation in the ultrasound diagnostic apparatus 1 is started, the ultrasound image S is displayed on the display unit 8 and the list N of measurement items is displayed so as to be superimposed on the ultrasound image S. In this example, abdominal aorta diameter, gallbladder size, and kidney size are displayed in the list N as measurement items N1 to N3, and the user can designate a measurement item by selecting one of the plurality of measurement items included in the list N.

Second Embodiment

In the measurement operation in the first embodiment, a plurality of measurement candidates are displayed on the display unit 8 in step S6. In a second embodiment, in a case where there is a measurement value exceeding a predetermined measurement standard range among the measurement values included in the measurement candidates, measurement candidates including measurement values outside the measurement standard range are highlighted on the display unit 8. For example, although not shown, in a case where the measurement item designated by the user through the operation unit 16 in step S1 in the first embodiment is the short axis diameter of the gallbladder, generally, there may be a tumor in the gallbladder in a case where the measurement value exceeds 40 mm. In this case, the measurement unit 9 highlights a measurement candidate having a measurement value exceeding 40 mm. In this case, the measurement unit 9 may display a text, which indicates that a measurement candidate having a measurement value exceeding 40 mm that is a predetermined reference value exceeds the reference value, so as to be superimposed on the ultrasound image.

As described above, by highlighting the measurement candidate having a measurement value outside the measurement standard range on the display unit 8, it becomes easier for the user to pay attention to the highlighted measurement candidate. As a result, it is possible to prevent the user from overlooking the measurement candidate.

Third Embodiment

In the first and second embodiments, a measurement candidate calculation standard that is stored in advance in the calculation standard storage unit 10 is used. In the third embodiment, the measurement candidate calculation standard is updated based on the reliability of the measurement line designated by the user through the operation unit 16.

Figure 6:
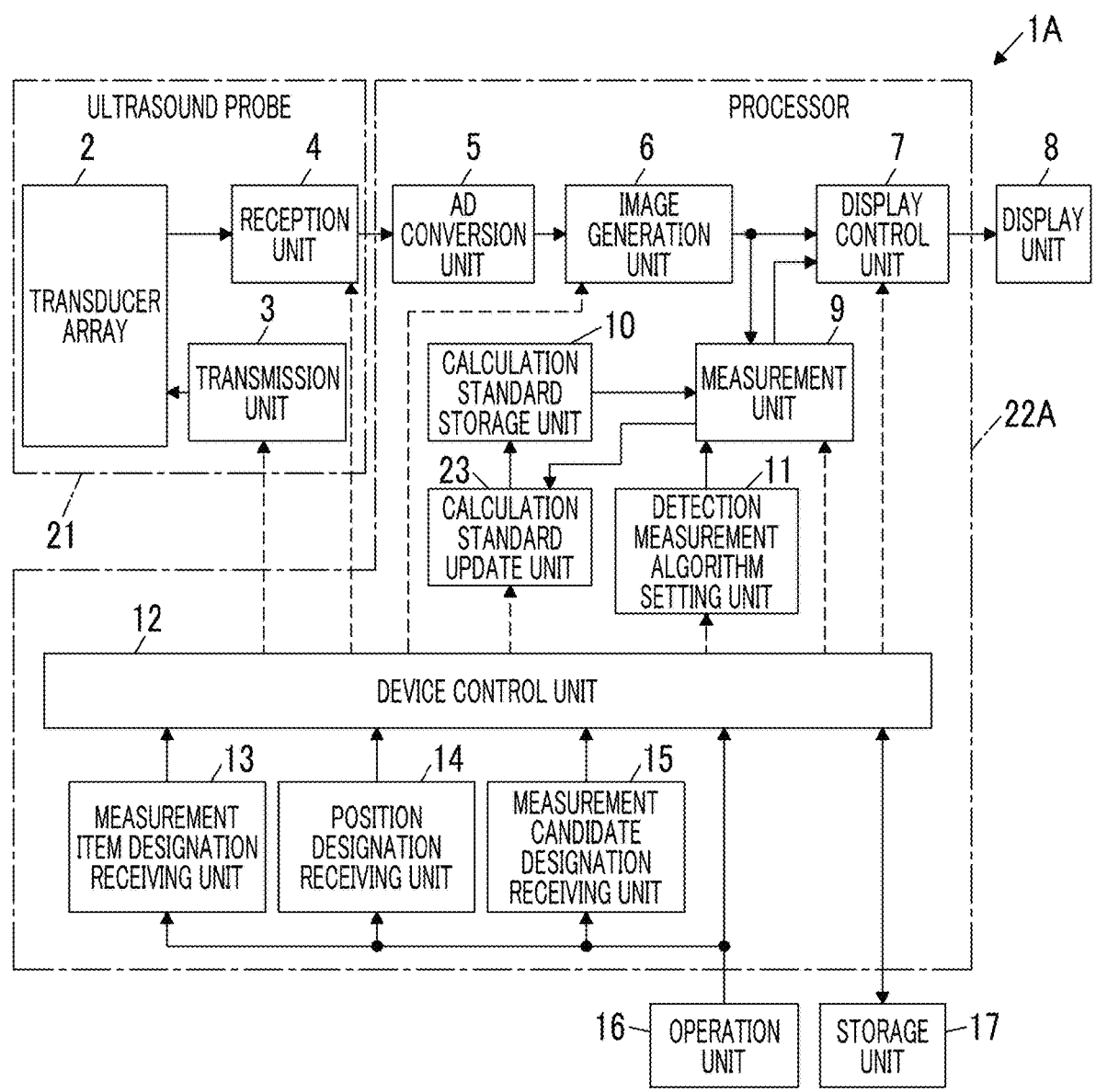
FIG. 6 is a block diagram showing the configuration of an ultrasound diagnostic apparatus according to a third embodiment of the present invention.

FIG. 6 shows the configuration of an ultrasound diagnostic apparatus 1A according to a third embodiment. The ultrasound diagnostic apparatus 1A according to the third embodiment is the same as the ultrasound diagnostic apparatus 1 according to the first embodiment except that a processor 22A has a calculation standard update unit 23. In the ultrasound diagnostic apparatus 1A according to the third embodiment, the calculation standard update unit 23 is connected to the calculation standard storage unit 10, and the measurement unit 9 and the device control unit 12 are connected to the calculation standard update unit 23.

The calculation standard update unit 23 updates the measurement candidate calculation standard based on the reliability of the designated measurement line in a case where a plurality of measurement lines are calculated by the measurement unit 9 and one measurement line is designated from the user through the operation unit 16. For example, in a case where a measurement operation is performed multiple times using the ultrasound diagnostic apparatus 1A, the calculation standard update unit 23 can update the threshold value of the reliability of the measurement line, which is stored in advance in the calculation standard storage unit 10, to any one of the average value, median value, minimum value, or the like of the reliability of a plurality of measurement lines designated by the user through the operation unit 16.

For example, in the case of updating the measurement candidate calculation standard, the user's designation results for a plurality of measurement lines in the plurality of ultrasound diagnostic apparatuses 1A may be collected, and the measurement candidate calculation standard may be updated based on the reliability of the measurement lines. Alternatively, the user's designation results for a plurality of measurement lines may be collected for each user and for each subject, and the measurement candidate calculation standard may be updated based on the reliability of the measurement lines.

In this manner, by reflecting the user's designation result in the measurement candidate calculation standard, it is possible to prevent a measurement line that is difficult to be designated by the user from being displayed on the display unit 8. Therefore, the user's preference can be reflected on the measurement result of the measurement target.

Fourth Embodiment

In the first to third embodiments, measurement results are obtained by selecting automatically calculated measurement candidates. In a fourth embodiment, the user can manually correct a measurement candidate.

Figure 7:
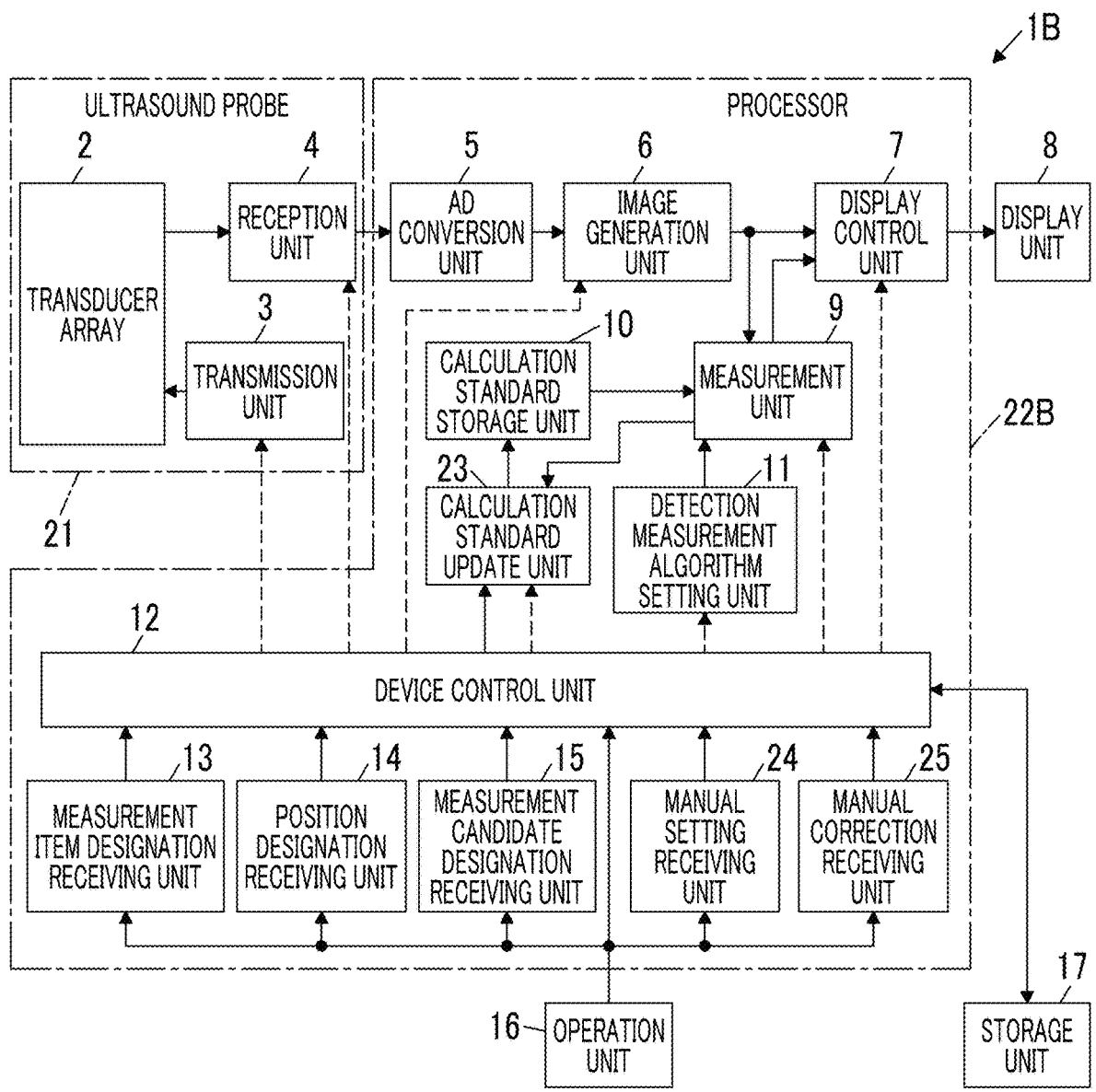
FIG. 7 is a block diagram showing the configuration of an ultrasound diagnostic apparatus according to a fourth embodiment of the present invention.

FIG. 7 shows the configuration of an ultrasound diagnostic apparatus 1B according to a fourth embodiment. The ultrasound diagnostic apparatus 1B according to the fourth embodiment is the same as the ultrasound diagnostic apparatus 1A according to the third embodiment except that a processor 22B has a manual setting receiving unit 24 and a manual correction receiving unit 25. In the ultrasound diagnostic apparatus 1B according to the fourth embodiment, the manual setting receiving unit 24 and the manual correction receiving unit 25 are connected to the device control unit 12, and the operation unit 16 is connected to the manual setting receiving unit 24 and the manual correction receiving unit 25.

The manual setting receiving unit 24 receives measurement line setting that is made by the user through the operation unit 16 for a measurement target received by the measurement item designation receiving unit 13. In addition, the manual setting receiving unit 24 transmits a command to the display control unit 7 through the device control unit 12 so that the measurement line set by the user through the operation unit 16 and the measurement value corresponding to the measurement line are displayed on the display unit 8.

The manual correction receiving unit 25 receives a correction made by the user through the operation unit 16 for the measurement line automatically calculated by the measurement unit 9.

Figure 8:
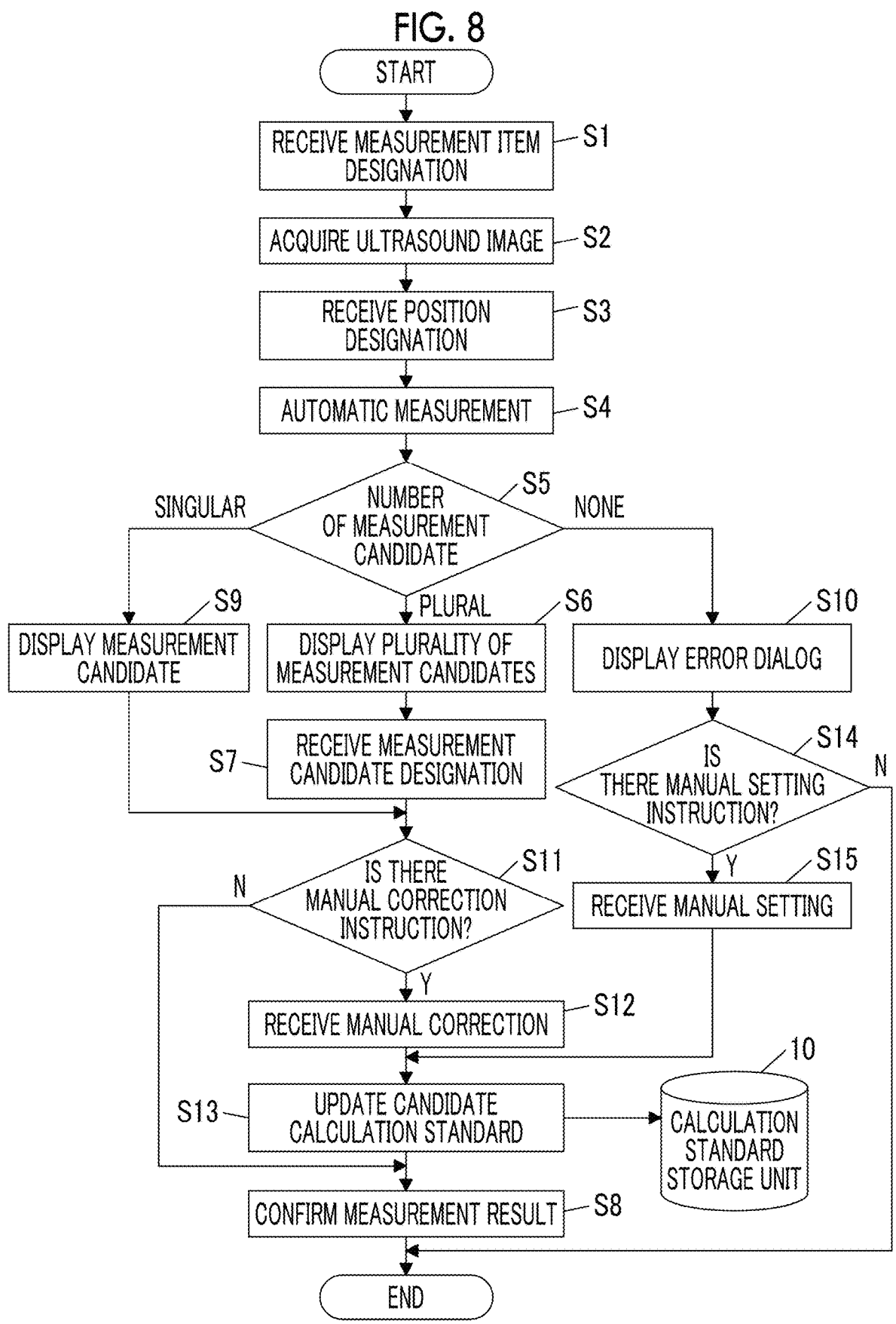
FIG. 8 is a flowchart showing a first measurement operation of the ultrasound diagnostic apparatus according to the fourth embodiment of the present invention.

Next, the measurement operation of the ultrasound diagnostic apparatus 1B in the fourth embodiment will be described with reference to the flowcharts shown in FIGS. 8 and 9. FIG. 8 shows a first measurement operation using the ultrasound diagnostic apparatus 1B. First, steps S1 to S5 are the same as steps S1 to S5 in the flowchart of the first embodiment shown in FIG. 3. In a case where it is determined that a plurality of measurement line candidates have been calculated in step S5, a plurality of measurement candidates are displayed on the display unit 8 in step S6, and designation of a measurement candidate from the user is received in the subsequent step S7. Steps S6 and S7 are the same as steps S6 and S7 in the flowchart of the first embodiment.

In a case where the designation of a measurement candidate from the user through the operation unit 16 is received in step S7, the process proceeds to step S11. In step S11, the user can manually correct the measurement candidate designated in step S7 through the operation unit 16. Manual correction indicates, for example, that the position of the measurement line is changed by the user through the operation unit 16 and that the position of the measurement point included in the measurement line is changed. In a case where the measurement candidate is manually corrected in step S11, the process proceeds to step S12 in which the manual correction result is received by the manual correction receiving unit 25.

In subsequent step S13, the calculation standard update unit 23 updates the calculation standard for the reliability of the measurement line based on the manual correction result received in step S12, and stores the update result in the calculation standard storage unit 10. For example, it is assumed that the measurement line is a line segment for measuring the length and the reliability is calculated by the sum of the first reliability based on the distance between the measurement line and the point designated by the user through the operation unit 16 in step S3 and the second reliability based on the edge likeness of the ultrasound image at the end point of the line segment. In this case, the calculation standard update unit 23 may update the reliability calculation standard so that the weight of the first reliability is increased in a case where the measurement line corrected by the user is closer to the point designated in step S3 than to the measurement line before correction and the weight of the second reliability is increased in a case where the measurement line corrected by the user is farther from the point designated in step S3 than from the measurement line before correction.

In a case where the calculation standard for the reliability of the measurement line is updated in step S13, the measurement result is confirmed in subsequent step S8, and the measurement operation in the ultrasound diagnostic apparatus 1B is ended.

In a case where it is determined that no manual correction has been made in step S11, the process proceeds to step S8, the measurement result is confirmed, and the measurement operation in the ultrasound diagnostic apparatus 1B is ended.

In a case where it is determined that only one measurement line has been calculated in step S5, the process proceeds to step S9 to display measurement candidates on the display unit 8. Step S9 is the same as step S9 in the first embodiment.

In a case where it is determined that no measurement line has been calculated in step S5, the process proceeds to step S10 to display an error dialog on the display unit 8, and the process proceeds to step S14.

In step S14, the user can manually set a measurement line on the ultrasound image through the operation unit 16. In a case where it is determined that the measurement line is manually set by the user in step S14, the process proceeds to step S15 in which the manual setting result of the measurement line is received by the manual setting receiving unit 24. In a case where the manual setting result of the measurement line is received in step S15, the process proceeds to step S13 to update the calculation standard for the reliability of the measurement line based on the manual setting result of the measurement line. In a case where the calculation standard for the reliability of the measurement line is updated in step S13, the measurement result is confirmed in step S8, and the measurement operation in the ultrasound diagnostic apparatus 1B is ended.

In a case where it is determined that no manual setting of measurement lines has been made in step S14, the measurement operation in the ultrasound diagnostic apparatus 1B ends at that point in time.

Next, the second and subsequent measurement operations of the ultrasound diagnostic apparatus 1B according to the fourth embodiment will be described. FIG. 9 is a flowchart showing the second and subsequent measurement operations.

Steps S1 to S3 are the same as steps S1 to S3 of the first measurement operation in the ultrasound diagnostic apparatus 1B. In a case where the position of the measurement target designated by the user through the operation unit 16 is received in step S3, the process proceeds to step S16.

In step S16, it is determined whether or not the calculation standard for the reliability of the measurement line has been updated in step S13 of the first measurement operation. Here, in a case where it is determined that the calculation standard for the reliability of the measurement line has been updated, the process proceeds to step S17.

In step S17, the measurement unit 9 reads out the calculation standard for the reliability of the measurement line updated in step S13 in the first measurement operation from the calculation standard storage unit 10. In subsequent step S4, the measurement unit 9 performs automatic measurement of the measurement target using the calculation standard for the reliability of the measurement line read out in step S17. Step S4 and subsequent step S5 are the same as steps S4 and S5 in the first measurement operation.

In a case where it is determined that a plurality of measurement line candidates have been calculated in step S5, the process proceeds to step S6. Steps S6 to S12 are the same as steps S6 to S12 in the first measurement operation. In a case where the result of manual correction made by the user through the operation unit 16 is received in step S12, the process proceeds to step S8 to confirm the measurement result, and the second and subsequent measurement operations in the ultrasound diagnostic apparatus 1B are ended.

In a case where it is determined that only one measurement line candidate has been calculated in step S5, the process proceeds to step S9. In a case where it is determined that no measurement line candidate has been calculated in step S5, the process proceeds to step S10. Steps S9 and S10 to S15 are the same as steps S9 and S10 to S15 in the first measurement operation.

As described above, according to the ultrasound diagnostic apparatus 1B of the fourth embodiment, the calculation standard for the reliability of the measurement line is updated based on the result of manual correction made by the user through the operation unit 16 for the calculated measurement candidate, and the calculation standard for the reliability of the measurement line is updated based on the result of the user's manual setting of the measurement line through the operation unit 16. Therefore, the accuracy of the measurement candidate calculated by the measurement unit 9 can be improved, and the measurement candidate reflecting the user's preference can be calculated.

In the fourth embodiment, the calculation standard for the reliability of the measurement line is updated in step S13 of the first measurement operation in the ultrasound diagnostic apparatus 1B, and the calculation standard for the reliability of the measurement line is not updated in the second and subsequent measurement operations. However, even in the second and subsequent measurement operations, the calculation standard for the reliability of the measurement line may be updated. In this case, for example, immediately after receiving the manual correction in step S12 in the second and subsequent measurement operations, the calculation standard for the reliability of the measurement line is updated as in step S13 shown in FIG. 8.

The ultrasound diagnostic apparatuses in the first to fourth embodiments are examples of the acoustic wave diagnostic apparatus.

Explanation of References 1, 1A, 1B: ultrasound diagnostic apparatus
2: transducer array
3: transmission unit
4: reception unit
5: AD conversion unit
6: image generation unit
7: display control unit
8: display unit
9: measurement unit
10: calculation standard storage unit
11: detection measurement algorithm setting unit
12: device control unit
13: measurement item designation receiving unit
14: position designation receiving unit
15: measurement candidate designation receiving unit 16: operation unit
17: storage unit
18: signal processing unit
19: DSC
20: image processing unit
21: ultrasound probe
22, 22A, 22B: processor
23: calculation standard update unit
24: manual setting receiving unit
25: manual correction receiving unit
L: measurement line
M: list
N: list
N1, N2, N3: measurement item
S: ultrasound image

What is claimed is:

1. An acoustic wave diagnostic apparatus, comprising:
a display unit that displays an acquired acoustic wave image;
an input device for a user to perform an input operation; and
a processor configured to:
receive designation of a measurement item relevant to a measurement target from the user through the input device;
set a detection measurement algorithm based on the received measurement item;
receive designation of a position of the measurement target on the acoustic wave image displayed on the display unit from the user through the input device;
detect the measurement target from the acoustic wave image based on the received position of the measurement target and the set detection measurement algorithm, measure the detected measurement target, calculate a measurement candidate based on a threshold value stored in a storage, and display the measurement candidate on the display unit; and
receive designation of the measurement candidate from the user through the input device in a case where a plurality of the measurement candidates are displayed on the display unit,
wherein the processor is further configured to use the received measurement candidate as a measurement result and update the threshold value stored in the storage based on a reliability corresponding to the received measurement candidate.

2. The acoustic wave diagnostic apparatus according to claim 1,
wherein the measurement candidate includes at least one of a measurement line used for measurement or a measurement value calculated for the measurement target, and the measurement line is displayed so as to be superimposed on the acoustic wave image.

3. The acoustic wave diagnostic apparatus according to claim 2,
wherein the measurement line is a line segment connecting two measurement points disposed at an edge of the measurement target or a closed curve drawn along the edge of the measurement target.

4. The acoustic wave diagnostic apparatus according to claim 3,
wherein the processor is further configured to detect the measurement target by recognition based on image processing, calculate a reliability of a recognition result based on at least one of edge likeness of the acoustic wave image at an end point of the line segment or a distance from the received position of the detected measurement target to the line segment, and display a plurality of the measurement candidates selected according to the calculated reliability on the display unit.

5. The acoustic wave diagnostic apparatus according to claim 4,
wherein the processor is further configured to change at least one of a color, a thickness, a line type, or a transparency for displaying the plurality of measurement candidates according to a value of the calculated reliability.

6. The acoustic wave diagnostic apparatus according to claim 5,
wherein the measurement candidate includes a plurality of measurement lines or a plurality of measurement values, and
wherein the processor is further configured to display both the plurality of measurement lines and the plurality of measurement values so as to be associated with each other in at least one of the color, the thickness, the line type, or the transparency.

7. The acoustic wave diagnostic apparatus according to claim 3,
wherein the processor is further configured to detect the measurement target by recognition based on image processing, calculate a reliability of a recognition result based on edge likeness of the acoustic wave image at an edge of the closed curve, and display a plurality of the measurement candidates selected according to the calculated reliability on the display unit.

8. The acoustic wave diagnostic apparatus according to claim 7,
wherein the processor is further configured to change at least one of a color, a thickness, a line type, or a transparency for displaying the plurality of measurement candidates according to a value of the calculated reliability.

9. The acoustic wave diagnostic apparatus according to claim 8,
wherein the measurement candidate includes a plurality of measurement lines or a plurality of measurement values, and
wherein the processor is further configured to display both the plurality of measurement lines and the plurality of measurement values so as to be associated with each other in at least one of the color, the thickness, the line type, or the transparency.

10. The acoustic wave diagnostic apparatus according to claim 1,
wherein the processor is further configured to receive manual correction of the calculated measurement candidate from the user through the input device.

11. The acoustic wave diagnostic apparatus according to claim 1,
wherein the processor is further configured to highlight the measurement candidate on the display unit in a case where a measurement value of the calculated measurement candidate is outside a predetermined measurement standard range.

12. The acoustic wave diagnostic apparatus according to claim 1,
wherein the processor is further configured to receive designation of at least one of a name of the measurement target, a name of a lesion, a name and measurement content of the measurement target, or a name and measurement content of a lesion as a measurement item relevant to the measurement target.

13. The acoustic wave diagnostic apparatus according to claim 1,
wherein the acoustic wave image is any one of an ultrasound image, a photoacoustic wave image, or a composite image of an ultrasound image and a photoacoustic wave image.

14. A control method of an acoustic wave diagnostic apparatus including:
a display unit that displays an acquired acoustic wave image;
an input device for a user to perform an input operation; and
a processor configured to:
receive designation of a measurement item relevant to a measurement target from the user through the input device;
set a detection measurement algorithm based on the received measurement item;
receive designation of a position of the measurement target on the acoustic wave image displayed on the display unit from the user through the input device;
detect the measurement target from the acoustic wave image based on the received position of the measurement target and the set detection measurement algorithm, measure the detected measurement target, calculate a measurement candidate based on a threshold value stored in a storage, and display the measurement candidate on the display unit; and
receive designation of the measurement candidate from the user through the input device in a case where a plurality of the measurement candidates are displayed on the display unit,
wherein the processor is further configured to use the received measurement candidate as a measurement result and update the threshold value stored in the storage based on a reliability corresponding to the received measurement candidate,
the control method comprising:
receiving the designation of the measurement item relevant to the measurement target from the user;
setting the detection measurement algorithm based on the received measurement item;
displaying the acoustic wave image;
receiving the designation of the position of the measurement target on the acoustic wave image from the user;
detecting the measurement target from the acoustic wave image based on the received position of the measurement target and the set detection measurement algorithm, measuring the detected measurement target, and calculating a measurement candidate based on a threshold value, and displaying the measurement candidate;
receiving the designation of the measurement candidate from the user in a case where the plurality of the measurement candidates are displayed;
using the received measurement candidate as the measurement result, and
updating the threshold value based on a reliability corresponding to the received measurement candidate.

* * * * *